(12) United States Patent
Yahiaoui et al.

(10) Patent No.: US 8,545,951 B2
(45) Date of Patent: Oct. 1, 2013

(54) ENDOTRACHEAL TUBES AND OTHER POLYMER SUBSTRATES INCLUDING AN ANTI-FOULING TREATMENT

(75) Inventors: Ali Yahiaoui, Roswell, GA (US); Brian J. Cuevas, Cumming, GA (US); Anthony Stephen Spencer, Woodstock, GA (US); Charles Edward Bolian, II, Buford, GA (US); David W. Koenig, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/408,528

(22) Filed: Feb. 29, 2012

(65) Prior Publication Data

US 2013/0220331 A1 Aug. 29, 2013

(51) Int. Cl.
*B29D 22/00* (2006.01)
(52) U.S. Cl.
USPC .......................................... 428/35.7; 604/245
(58) Field of Classification Search
USPC ......................... 428/35.7; 605/245; 424/489
See application file for complete search history.

(56) References Cited

U.S. PATENT DOCUMENTS

| | | |
|---|---|---|
| 3,434,869 A | 3/1969 | Davidson et al. |
| 4,111,922 A | 9/1978 | Beede et al. |
| 4,210,206 A | 7/1980 | Ely et al. |
| 4,311,573 A | 1/1982 | Mayhan et al. |
| 4,499,154 A | 2/1985 | James et al. |
| 4,548,844 A | 10/1985 | Podell et al. |
| 4,575,476 A | 3/1986 | Podell et al. |
| 4,667,661 A | 5/1987 | Scholz et al. |
| 4,717,378 A | 1/1988 | Perrault et al. |
| 4,774,937 A | 10/1988 | Scholz et al. |
| 4,856,502 A | 8/1989 | Ersfeld et al. |
| 4,876,126 A | 10/1989 | Tanabe et al. |
| 4,942,193 A | 7/1990 | Van Buskirk et al. |
| 4,968,532 A | 11/1990 | Janssen et al. |
| 5,069,965 A | 12/1991 | Esemplare |
| 5,081,174 A | 1/1992 | VanBuskirk |
| 5,229,172 A | 7/1993 | Cahalan et al. |
| 5,229,450 A | 7/1993 | Van Buskirk et al. |
| 5,246,012 A | 9/1993 | Strickland |
| 5,260,093 A | 11/1993 | Kamel et al. |

(Continued)

FOREIGN PATENT DOCUMENTS

| | | |
|---|---|---|
| EP | 191471 | 8/1986 |
| WO | WO 9206694 | 4/1992 |

(Continued)

OTHER PUBLICATIONS

Bacteria, Biolfims, Antibiotic Resistance and Infections 84, last updated Jun. 26, 2011.

(Continued)

*Primary Examiner* — N. Edwards
(74) *Attorney, Agent, or Firm* — Dority & Manning, P.A.

(57) ABSTRACT

Anti-fouling treatments are applied to polymer substrates for preventing bacterial adhesion. The polymer substrate may comprise a medical device, such as a catheter. The treatment generally comprises a polymer layer graft polymerized to the surface of the polymer substrate. An anti-biofilm agent is contained in the polymer layer or applied to the surface. A polymer over-layer is then applied that encapsulates the anti-biofilm agent. The anti-biofilm agent prevents bacterial adhesion through the polymer over-layer.

24 Claims, 4 Drawing Sheets

(56) References Cited

U.S. PATENT DOCUMENTS

| | | |
|---|---|---|
| 5,264,249 A | 11/1993 | Perrault et al. |
| 5,272,012 A | 12/1993 | Opolski |
| 5,326,584 A | 7/1994 | Kamel et al. |
| 5,344,455 A | 9/1994 | Keogh et al. |
| 5,364,662 A | 11/1994 | Domenico et al. |
| 5,395,666 A | 3/1995 | Brindle |
| 5,405,666 A | 4/1995 | Brindle |
| 5,470,625 A | 11/1995 | Perrault |
| 5,474,768 A | 12/1995 | Robinson |
| 5,476,509 A | 12/1995 | Keogh et al. |
| 5,509,899 A | 4/1996 | Fan et al. |
| 5,571,219 A | 11/1996 | Gorton |
| 5,611,336 A | 3/1997 | Page et al. |
| 5,693,034 A | 12/1997 | Buscemi et al. |
| 5,742,943 A | 4/1998 | Chen |
| 5,800,685 A | 9/1998 | Perrault |
| 5,993,972 A | 11/1999 | Reich et al. |
| 6,001,894 A | 12/1999 | Ottersbach et al. |
| 6,039,940 A | 3/2000 | Perrault et al. |
| 6,045,732 A | 4/2000 | Nakatsuji et al. |
| 6,083,393 A | 7/2000 | Wu et al. |
| 6,242,042 B1 | 6/2001 | Goldstein et al. |
| 6,287,285 B1 | 9/2001 | Michal et al. |
| 6,306,514 B1 | 10/2001 | Weikel et al. |
| 6,331,509 B1 | 12/2001 | Heimann et al. |
| 6,345,394 B1 | 2/2002 | Nakamura et al. |
| 6,347,246 B1 | 2/2002 | Perrault et al. |
| 6,358,557 B1 | 3/2002 | Wang et al. |
| 6,468,649 B1 | 10/2002 | Zhong |
| 6,509,098 B1 | 1/2003 | Merrill et al. |
| 6,632,470 B2 | 10/2003 | Morra et al. |
| 6,656,517 B2 | 12/2003 | Michal et al. |
| 7,220,491 B2 | 5/2007 | Rouns et al. |
| 7,455,892 B2 * | 11/2008 | Goodwin et al. ............ 427/578 |
| 7,678,716 B2 * | 3/2010 | Yahiaoui et al. ................ 442/63 |
| 7,816,412 B2 * | 10/2010 | Yahiaoui et al. ................ 516/99 |
| 8,017,042 B2 | 9/2011 | Copp-Howland |
| 2003/0091612 A1 | 5/2003 | Sabesan |
| 2004/0151930 A1 | 8/2004 | Rouns et al. |
| 2005/0118239 A1 | 6/2005 | Sabesan |
| 2006/0177490 A1 | 8/2006 | Massouda |
| 2006/0180552 A1 | 8/2006 | Downs |
| 2007/0048356 A1 | 3/2007 | Schorr et al. |
| 2007/0048358 A1 | 3/2007 | Schorr et al. |
| 2008/0063693 A1 | 3/2008 | Cook et al. |
| 2008/0147019 A1 * | 6/2008 | Song et al. .................... 604/265 |
| 2009/0162439 A1 | 6/2009 | Gobin |
| 2009/0318622 A1 | 12/2009 | Migonney et al. |
| 2010/0147309 A1 | 6/2010 | Cuevas et al. |
| 2011/0305909 A1 | 12/2011 | Weaver et al. |

FOREIGN PATENT DOCUMENTS

| | | |
|---|---|---|
| WO | WO 9639204 | 12/1996 |
| WO | WO 9926683 | 6/1999 |
| WO | WO 0012100 | 3/2000 |
| WO | WO 0061205 | 10/2000 |
| WO | WO 0222186 | 3/2002 |
| WO | WO 02053664 | 7/2002 |
| WO | WO 03000116 | 1/2003 |
| WO | WO 2007/120631 | 10/2007 |
| WO | WO 2007/141460 | 12/2007 |
| WO | WO 2008/075222 | 6/2008 |

OTHER PUBLICATIONS

N-Vinylpyrrolidone—Wikipedia, last modified Oct. 27, 2011.
Antimicrobial surfaces—Wikipedia, last modified Jan. 3, 2012.
Dimethyl sulfoxide—Wikipedia, last modified Mar. 18, 2013.
N,N'-Methylenebisacrylamide—Wikipedia, last modified Apr. 18, 2011.

* cited by examiner

ENDOTRACHEAL TUBES AND OTHER POLYMER SUBSTRATES INCLUDING AN ANTI-FOULING TREATMENT

BACKGROUND

Various materials used in medical devices are designed to be inserted into a patient to assist in patient care. For example, tracheal tubes like endotracheal tubes are designed to be inserted through the mouth and throat of a patient for assisting in respiration while tracheal tubes like tracheostomy tubes are inserted through the throat for the same purpose. Further, other devices, such as tracheal suction devices are used in conjunction with tracheal tubes to, for instance, remove accumulated secretions from the lungs of a patient. In addition to the above catheters, various other medical devices and instruments are designed to be inserted into other areas of the body. For example, catheters are also used in conjunction with the urinary tract, the digestive system, and in various other places.

Also, materials can be used in applications where they come in contact with biological media including biological tissues and fluids (blood, urine, menses) and where there is a need to prevent onset of bacterial adhesion and proliferation. These materials can be used in various health and hygiene applications such as diapers, adult incontinence, feminine hygiene pads, wipers, sponges, etc.

One problem that arises with the use of materials that come in contact with biological media is, after extended lengths of time, the surfaces of the material or walls are susceptible to bacterial colonization. Bacterial colonization can lead to the generation of bacterial bio-film communities that can subsequently enter the body of a patient and colonize. Depending upon the type of microorganisms present, bacterial colonization within the patient can lead to infection and illness.

For instance, one type of illness associated with the use of catheters, particularly endotracheal tubes, is Ventilator Associated Pneumonia (VAP). Ventilator Associated Pneumonia is pneumonia that develops 48 hours or longer after a patient has been placed on a ventilator through the use of a tracheal tube, more commonly an endotracheal tube. Ventilator Associated Pneumonia is caused by microorganisms colonizing in the lower respiratory tract. Although the microorganisms can infiltrate the body of the patient by numerous different ways, it is believed that, in some cases, the infection is initially caused by bacterial colony growth on the interior walls of the tracheal tube. In particular, the incidence of Ventilator Associated Pneumonia has been shown to increase with the patient's time on a ventilator, also sometimes called a respirator.

In view of the above, a need currently exists for a treatment of materials that are used in medical device applications that is capable of preventing onset of bacterial biofilm on those materials. In addition there is a need to develop anti-infection methods that do not rely on a kill mechanism like currently available anti-microbial and antibiotics do. A problem with the kill mechanism is that pathogens will eventually develop a resistance to antimicrobials. A well known example of a resistant or hard to kill bacteria is methicillin-resistant *Staphylococcus aureus* (or MRSA)

SUMMARY

In general, the present disclosure is directed to surface modification methods and surface chemistry compositions for improved biocompatibility and reduced bio-fouling. More particularly, the present disclosure is directed to an anti-fouling surface treatment that inhibits bacteria from colonizing on the surface and forming a bio-film. The surface treatment is particularly well suited for use in medical devices, such as catheters and health and hygiene products (diapers, wipes, feminine hygiene pads, sponges, etc).

In one embodiment, the surface treatment includes surface activation of a substrate to possibly remove surface contaminates and weak boundary layers. Selected monomers are then graft polymerized on the surface of the polymer substrate. In one embodiment, for instance, the graft polymerization may be radiation-induced. In one embodiment, a hydrogel polymer is formed on the surface of the polymer substrate that is hydrophilic. As used herein, a hydrogel polymer is a network of polymer chains, that sometimes exist as a colloidal gel, in which water is the dispersion medium. Hydrophilic materials, on the other hand, generally refer to materials that have an affinity for water. Some hydrophilic materials readily absorb water or dissolve in water.

An anti-biofilm agent is associated with the graft polymerized layer. The anti-biofilm agent, for instance, may be combined with the monomers used during graft polymerization or may be applied to the hydrophilic layer after formation. A polymer over-layer is then applied which encapsulates the anti-biofilm agent without inhibiting its effectiveness.

In one particular embodiment, for instance, the present disclosure is directed to an article including an anti-fouling treatment. The article includes a polymer substrate having a first surface. In one embodiment, the first surface of the polymer substrate is treated with a plasma glow discharge ("plasma"). For instance, the first surface may be plasma oxidized in the presence of oxygen. A hydrophilic layer is graft polymerized to the first surface of the polymer substrate. The hydrophilic layer can be made from one or more monomers. In one embodiment, the hydrophilic layer may comprise a hydrogel polymer that has been graft polymerized to the first surface by being subjected to irradiation. Monomers that may be used to produce the hydrophilic layer include acrylamido methyl propane sulfonic acid or a salt thereof, N,N-dimethyl amino ethyl acrylate dimethyl sulfate quaternary, dimethyl amino ethyl methacrylate, acrylic acid, methacrylic acid, acrylamide, N-(3-aminopropyl) methacrylamide hydrochloride, hydroxyethyl methacrylate, styrene sulfonic acid, potassium sulfopropyl acrylate, dimethylacrylamide, dimethyl amino ethyl methacrylate or their salts or mixtures thereof. In addition to one or more of the above monomers, the hydrophilic layer may also include a crosslinking agent and an initiator.

In accordance with the present disclosure, an anti-biofilm agent is associated with the hydrophilic layer. The anti-biofilm agent is present at the top surface of the hydrophilic layer, may be contained within the hydrophilic layer and/or may be applied to the top surface of the hydrophilic layer as a separate layer. In one embodiment, the anti-biofilm agent comprises a metal or a metal alloy, such as a silver alloy. In one embodiment, the anti-biofilm agent comprises silver sodium zirconium phosphate dispersed in a polyvinylpyrrolidone polymer.

The anti-fouling treatment of the present disclosure further includes a polymer over-layer positioned on the hydrophilic layer and encapsulating the anti-biofilm agent. The polymer over-layer, for instance, may comprise a cationic polymer wherein the hydrophilic layer may be anionic or vice versus. In one embodiment, the polymer over-layer comprises a chitosan, such as chitosan glycolate. The polymer over-layer can generally have a dry thickness of less than about 100 micrometers ("micron"), such as from about 0.1 microns to about 80 microns.

In accordance with the present disclosure, the anti-biofilm agent is present in the anti-fouling treatment in an amount sufficient to inhibit bacteria from attaching to an exterior surface of the article. Of particular advantage, it was discovered that the anti-biofilm agent is effective in preventing bacteria from attaching to an exterior surface of the article while still remaining encapsulated within the polymer over-layer. In one embodiment, the anti-biofilm agent is present in the anti-fouling treatment in an amount effective to prevent bacterial attachment but in an amount insufficient to kill the bacteria. The amount the anti-biofilm agent is present in the anti-fouling treatment in order to prevent bacterial attachment without killing or destroying bacteria may depend upon various factors. In one embodiment, for instance, the anti-biofilm agent may be present in the anti-fouling treatment from a positive amount to an amount less than about 0.2% by weight, such as in an amount less than about 0.18% by weight, such as in an amount less than about 0.16% by weight, such as in an amount less than about 0.14% by weight, such as in an amount less than about 0.12% by weight, such as in an amount less than about 0.1% by weight. In general, the anti-biofilm agent is present in the anti-fouling treatment in an amount greater than about 0.0001% by weight, such as in an amount greater than about 0.001% by weight.

In one embodiment, the article may comprise a catheter, such as a tracheal tube. The catheter may include a tubular structure defining a lumen. The treatment may comprise a lining for the lumen.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
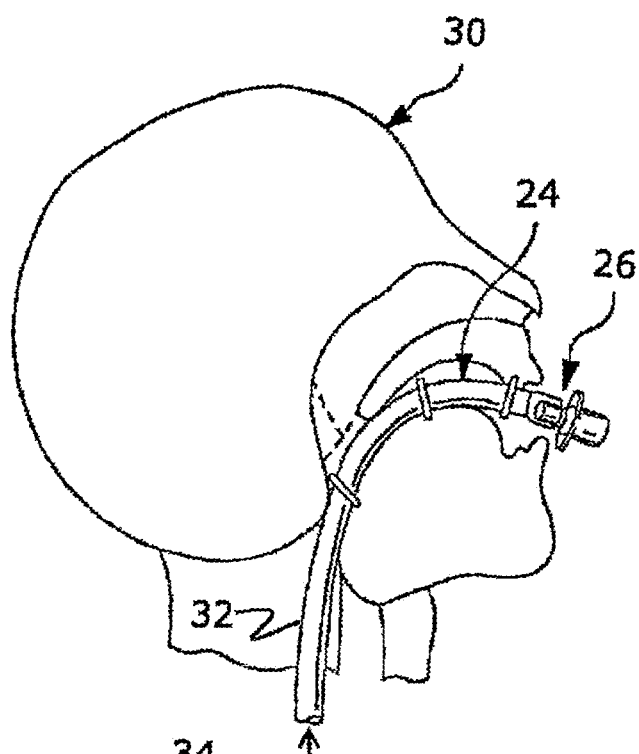
FIG. 1 is a perspective view of one embodiment of a respiratory device made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

The present disclosure is generally related to an anti-fouling treatment for polymer substrates. The treatment of the present disclosure inhibits microorganisms, such as bacteria, from attaching to a surface of the substrate. Thus, bacteria colony growth is inhibited which prevents the formation of a biofilm. In general, any suitable polymer substrate may be treated in accordance with the present disclosure. The treatment is particularly well suited for use on medical instruments that include polymer components. For example, in one embodiment, the treatment may be applied to the inside lining of a tubular structure defined by a catheter.

The anti-fouling treatment of the present disclosure generally comprises an initial layer that is graft polymerized to the surface of a polymer substrate. An anti-biofilm agent is contained in the polymer layer or is applied to the top of the polymer layer. In accordance with the present disclosure, a polymer over-layer is then applied such that the biofilm agent is encapsulated within the structure. The polymer over-layer is constructed so as to have characteristics that allow the anti-biofilm agent to inhibit bacterial growth on an exterior surface of the polymer over-layer, i.e. the polymer over-layer does not adversely interfere with the ability of the anti-biofilm agent to inhibit bacterial growth. In one embodiment, for instance, the polymer over-layer contains a chitosan.

As described above, the anti-fouling treatment of the present disclosure is particularly well suited for use in medical devices, such as catheters.

For purposes of illustration, FIG. 1 illustrates one embodiment of a catheter that may be made in accordance with the present disclosure. More particularly, FIG. 1 illustrates an endotracheal tube 24 that has been placed in the mouth and throat of a patient 30. In the embodiment illustrated, the endotracheal tube 24 includes a fitting 26 which is adapted to engage a ventilator or other similar device as part of an overall respiratory device.

In an alternative embodiment, instead of being attached to a respirator, the tracheal tube may also be attached to an aspirating catheter tube which is intended to be connected to a vacuum source for removing secretions from a patient's lungs.

As shown in FIG. 1, the endotracheal tube 24 includes a tubular structure 32 that defines a lumen 34. As described above, the lumen 34 can be used to feed oxygen into the lungs of the patient or to provide a suction force for removing secretions. In an analogous manner, a tracheostomy tube is inserted directly into the trachea through a stoma created in the throat and tracheal wall by surgical means and enters the trachea below the glottis. Both types of tube have a relatively large main ventilating lumen 34 that delivers the air from the mechanical ventilating device to the lungs.

In accordance with the present disclosure, the tubular structure 32 is subjected to an anti-fouling treatment that prevents bacteria from attaching to the walls of the tubular structure. The anti-fouling treatment, for instance, may comprise a lining that surrounds the lumen 34. It should be understood, however, that the anti-fouling treatment may also be applied to the exterior surface of the tubular structure as well. In one embodiment, both the inside and outside surfaces of the endotracheal tube may be treated in accordance with the present disclosure.

Figure 2:
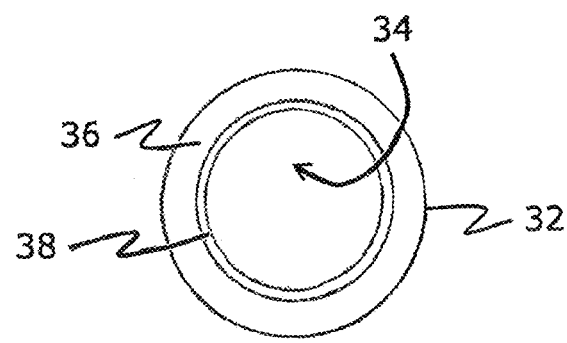
FIG. 2 is a cross-sectional view of a portion of the respiratory device illustrated in FIG. 1.

Referring to FIG. 2, a cross-sectional view of the tubular structural 32 shown in FIG. 1 is illustrated. As shown, the tubular structure 32 defines the lumen 34 and includes a tubular wall 36 that is lined in accordance with the present disclosure with an anti-fouling treatment 38.

Although an endotracheal tube is shown in FIGS. 1 and 2, it should be understood that the anti-fouling treatment of the present disclosure may be applied to various other medical devices. For instance, the anti-fouling treatment may be applied to any medical device made from a polymer that is capable of accepting the anti-fouling treatment, such as any suitable catheter including enteral feeding tubes. In addition to medical devices, it should also be understood that any suitable polymer substrate may be treated in accordance with the present disclosure. For instance, other materials and medical devices that may be treated in accordance with the present disclosure include prosthetic devices and implants including shoulder, knee and hip replacements, artificial valves, dental implants, contact lenses, ocular implants, surgical instrumentation, medical tubing and accessories and the like. In addition to the above, various health and hygiene products may also be treated in accordance with the present disclosure. Such products may include, for instance, wound care dressings and bandages and absorbent articles, such as diapers, feminine hygiene products, adult incontinence products, sponges, wipes, and the like.

The tubular wall 36 as shown in FIG. 2 can be made from various different polymers. In one embodiment, for instance, the polymer wall may be made from a silicone or a polyurethane. In an alternative embodiment, the polymer wall may be made from a polyvinyl chloride polymer. Other polymers that may be used to construct all or a portion of the tubular wall 36 include polyamides, polycarbonates, polyethers, polyesters, polyolefins including polyethylenes and polypropylenes, polystyrenes, polyisoprenes, fluorocarbons such as polytetrafluoroethylenes, copolymers thereof, and mixtures thereof.

Figure 3:
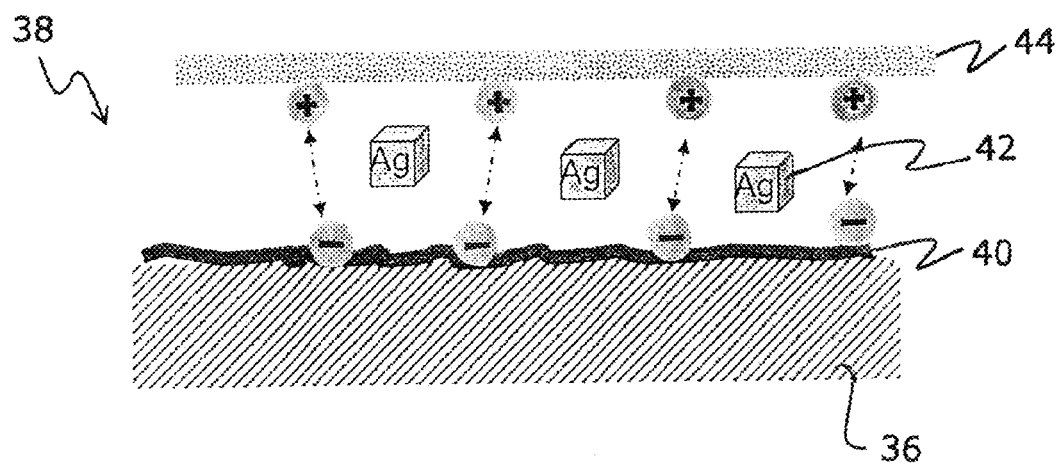
FIG. 3 is a diagram illustrating one embodiment of an anti-fouling treatment in accordance with the present disclosure.

Referring to FIG. 3, a simplified illustration of the anti-fouling treatment of the present disclosure is illustrated. As shown, the anti-fouling treatment 38 is attached to the surface of a polymer substrate 36. The polymer substrate 36, for instance, may comprise the tubular structure illustrated in FIG. 2. In accordance with the present disclosure, the anti-fouling treatment generally includes a base layer 40 that comprises a polymer that has been graft polymerized to the surface of the polymer substrate 36. In one embodiment, the layer 40 may comprise a hydrogel polymer that is anionic in character. The polymer layer 40 is shown in association with an anti-biofilm agent 42. In the embodiment illustrated, the anti-biofilm agent 42 comprises silver particles, such as silver nanoparticles.

The anti-fouling treatment 38 further includes a polymer over-layer 44 (not drawn to scale). The polymer over-layer 44 encapsulates the anti-biofilm agent 42 within the anti-fouling treatment 38. In one embodiment, the polymer over-layer 44 is cationic in character such that it forms a bonding attraction with the polymer layer 40. The polymer over-layer 44 is made from a polymer and has a thickness such that the polymer over-layer encapsulates the anti-biofilm agent 42 without adversely impacting its effectiveness in inhibiting bacteria from attaching to the exterior surface of the anti-fouling treatment 38 which, in one embodiment, is the exterior surface of the over-layer. As will be described in greater detail below, the polymer over-layer 44 serves to encapsulate the anti-biofilm agent without inhibiting its effectiveness.

In order to produce the anti-fouling treatment of the present disclosure, in one embodiment, the surface of the polymer substrate may be optionally cleaned, activated or otherwise modified in order to receive the polymer layer 40 as shown in FIG. 3. For example, in one embodiment, the surface of the polymer substrate can be subjected to a plasma. The plasma, for instance, may cause oxidation of the surface. Subjecting the surface of the polymer substrate to plasma, such as radio frequency plasma, can prime the surface by removing contaminants, weak boundary layers, and heterogeneities. Surface activation can also introduce polar groups that may later bond to the anti-fouling treatment.

In addition to plasma treatment, the surface of the polymer substrate may be activated or primed in various other ways. For instance, in other embodiments, the surface of the polymer substrate may be subjected to corona discharge, flame, peroxidation, laser annealing, ionizing radiation, and mixtures thereof. In still other embodiments, the polymer substrate may include additives or be coextruded with additives that migrate to the surface of the polymer and provide surface functionality for better bonding to the anti-fouling treatment. In still another embodiment, the polymer substrate can be formed from a blend of polymers that can segregate to form controlled microstructures and surface functionalities.

Once the surface of the polymer substrate is primed or activated (if desired), the surface of the polymer substrate is graft polymerized with a polymer layer. In one embodiment, for instance, the polymer layer graft polymerized with the polymer substrate may comprise a hydrophilic layer, such as a hydrogel polymer.

Graft polymerization can occur using various different procedures and techniques. In one embodiment, for instance, one or more monomers are contacted with the surface of the polymer substrate and subjected to irradiation in an amount sufficient for graft polymerization to occur. The surface of the polymer substrate can be irradiated using, for instance, electron beam energy, gamma rays, ultraviolet light, x-rays, and combinations thereof. Graft polymerization of the monomers to the polymer surface can result in the formation of covalent bonds thus making the anti-fouling treatment of the present disclosure wear resistant and non-leachable.

Various different types of monomers can be used to produce the initial polymer layer on the polymer substrate. In one embodiment, for instance, the polymer layer is formed from acrylamido methyl propane sulfonic acid or a salt thereof. Other monomers that may be used to form the polymer layer include N,N-dimethylaminoethyl acrylate dimethyl sulfate quaternary, dimethyl amino ethyl methacrylate, acrylic acid, methacrylic acid, acrylamide, N-(3-aminopropyl) methacrylamide hydrochloride, hydroxyethyl methacrylate, styrene sulfonic acid, potassium sulfopropyl acrylate, dimethylacrylamide, dimethyl amino ethyl methacrylate or their salts or mixtures thereof.

In one embodiment, the polymer layer is formed from acrylamido methyl propane sulfonic acid or a salt thereof combined with one or more of the other monomers described above. For instance, the monomer composition may further contain N-vinylpyrrolidone.

In addition to one or more monomers, the composition applied to the surface of the polymer substrate may also comprise one or more solvents, a crosslinking agent, and/or an initiator.

The solvent that can be present in the composition may comprise water, an organic solvent such as a polar aprotic solvent, or mixtures thereof. The particular solvent selected and the amount present in the composition can depend upon the other components contained in the composition. In one embodiment, the composition may contain water in combination with dimethyl sulfoxide or glycerine. Water can be present in the composition, for instance, in an amount from about 5% to about 90% by weight, such as in an amount from about 10% to about 60% by weight and from about 20% to about 45%. If present, the polar aprotic solvent may be present in an amount from about 0.5% to about 10% by weight, such as in an amount from about 1% to about 5% by weight.

The crosslinking agent contained in the composition depends upon the monomers present. In one embodiment, for instance, the crosslinking agent may comprise N,N'-methylene bisacrylamide. The crosslinking agent is generally present in an amount less than 3% by weight, such as in an amount from about 0.01 to about 0.5% by weight.

Examples of initiators which may be used include IRGACURE® 184 (1-hydroxycyclohexyl phenyl ketone), IRGACURE® 2959 (4-(2-hydroxyethoxy)phenyl-(2-hydroxy-2- methylpropyl)ketone)), and DAROCURE® 1173.alpha.-hydroxy-.alpha., .alpha.-dimethylacetophenone), all commercially available from Ciba Specialty Chemicals. These initiators are desired because they are non-yellowing. Additional examples of suitable initiators (which may be photo initiators or thermal initiators) may include benzoyl peroxide, azo-bis-isobutyro-nitrile, di-t-butyl peroxide, bromyl peroxide, cumyl peroxide, lauroyl peroxide, isopropyl percarbonate, methylethyl ketone peroxide, cyclohexane peroxide, tutylhydroperoxide, di-t-amyl peroxide, dicumyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), actophenones (such as acetophenone, trichloroacetophenone, 2,2-diethoxyacetophenone, p-t-butyl-trichloro-acetophenone, 2,2-dimethoxy-2-phenyl-acetophenone, and p-dimethylaminoacetophenone), thioxanthones (such as xanthone, thioxanthone, 2-chlorothioxanthone, and 2-isopropylthioxanthone), benzyl 2-ethyl anthraquinone, methylbenzoyl formate, 2-hydroxy-2-methyl-1-phenylpropane-1-one, 2-hydroxy-4'-isopropyl-2-methyl propiophenone, .alpha.-hydroxy ketone, tetramethyl thiuram monosulfide, allyl diazonium salt, and combinations of camphorquinone and ethyl 4-(N,N-dimethylamino)benzoate.

The initiator can be present in the composition in minor amounts. For instance, one or more initiators may be present in the composition in an amount from about 0.01% to about 5% by weight, such as from about 0.05% to about 2% by weight.

The one or more monomers may be present in the composition generally in an amount from about 10% to about 80% by weight, such as in an amount from about 30% to about 70% by weight. The above amounts refer to the total amount of monomers present. If a blend of monomers are used, the proportionate amounts of each monomer can vary.

In order to form the polymer layer 40 as shown in FIG. 3, the composition is applied to the surface of the polymer substrate and polymerization is initiated which causes the monomers to polymerize and graft to the surface of the substrate. For instance, in one embodiment, the surface of the substrate can be irradiated while being contacted with the composition. The amount of energy used during graft polymerization can vary. For instance, the surface can be irradiated from a UV source at an energy level of from about 0.1 J/cm$^2$ to about 3 J/cm$^2$, such as from about 0.3 J/cm$^2$ to about 1 J/cm$^2$. The energy may also be supplied in the form a source of gamma rays, or an electron beam.

The surface graft polymerization of monomer(s) takes place via radical initiation and propagation mechanisms.

As described above, in one embodiment, graft polymerization is initiated using ionizing radiation or electron beam. In other embodiments, however, graft polymerization can occur using chemical initiation such as through redox reactions or through peroxide initiation. In still other embodiments, the monomer solution may comprise other species, such as oligomers, that become an integral part of the surface graft on the polymer. In still another embodiment, the monomers may comprise charged species that provide ionic interactions with the surface of the substrate.

In accordance with the present disclosure, the polymer layer 40 as shown in FIG. 3 is constructed so as to be in association with one or more anti-biofilm agents 42. In one embodiment, at least a portion of the anti-biofilm agent is present at a surface of the polymer layer 40. In general, the anti-biofilm agent may be incorporated into the monomer composition used to produce the polymer layer 40, can be added to the polymer layer 40 during polymerization, or can be applied to the polymer layer 40 as a separate layer.

Various different anti-biofilm agents may be incorporated into the anti-fouling treatment depending upon the particular application and the end use for the polymer substrate. In one embodiment, the anti-biofilm agent may comprise a metal or a metal alloy. Such metals include silver ions, copper ions, and/or zinc ions. In one embodiment, metal particles are incorporated into the anti-fouling treatment that are less than one micron in size. For instance, the metal particles may have an average diameter of less than about one micron, such as less than about 0.8 microns, such as less than about 0.3 microns. The particles are generally larger than 0.001 microns.

In one embodiment, the anti-biofilm agent may comprise metal particles or metal ions that are associated with a carrier, such as an inorganic carrier. The carrier may comprise a phosphate, such as a zirconium phosphate, calcium phosphate, aluminum phosphate, or may comprise hydroxyl apatite, a zeolite, a silica gel, or a glass. In one particular embodiment, the anti-biofilm agent may comprise silver sodium hydrogen zirconium phosphate.

In addition to metal ions or instead of metal ions, various other anti-biofilm agents may be used. For instance, in one embodiment, a quaternary ammonium compound may be present. For instance, the quaternary ammonium compound may comprise a quaternary ammonium siloxane or a polyquaternary amine. Other anti-biofilm agents include halogens, such as bromine compounds, chlorine compounds, and the like. Various anti-biofilm agents include chlorine dioxide, a thiazole, a thiocyanate, an isothiazolin, a cyanobutane, a dithiocarbamate, a thione, a triclosan, an alkylsulfosuccinate, an alkyl-aminoalkyl glycine, a dialkyl-dimethyl-phosphonium salt, a cetrimide, hydrogen peroxide, 1-alkyl-1,5-diazapentane, or cetyl pyridinium chloride.

The amount of anti-biofilm agent present within the anti-fouling treatment can depend upon numerous factors including the different components contained in the treatment, the end use for the polymer substrate, the type of bacteria that may come in contact with the polymer substrate, and the like. In general, the anti-biofilm agent is present in the anti-fouling treatment in an amount effective to inhibit bacteria from attaching to an exterior surface of the anti-fouling treatment. In one embodiment, however, the anti-biofilm agent may be present in an amount insufficient to kill bacteria. In certain embodiments, for instance, there may be benefits to only inhibiting attachment as opposed to using a bactericide. Using a material in a concentration sufficient to kill bacteria, for instance, may cause the bacteria to become resistant to the anti-fouling treatment over time.

In one embodiment, the anti-biofilm agent is present in the anti-fouling treatment in an amount less than about 0.2% by weight, such as in an amount less than about 0.18% by weight, such as in an amount less than about 0.16% by weight. In other embodiments, the anti-biofilm agent is present in the treatment in an amount less than about 0.14% by weight, such as in an amount less than about 0.12% by weight, such as in an amount less than about 0.1% by weight. For most applications, the anti-biofilm agent is present in the treatment in an amount greater than about 0.0001% by weight, such as in an amount greater than about 0.001% by weight, such as in an amount greater than about 0.01% by weight. The above weight percentages refer to the dried coating weight.

As described above, the anti-biofilm agent may be incorporated into the polymer layer 40 or may be applied to the polymer layer 40. In one particular embodiment, the anti-biofilm agent may comprise a silver alloy that is dispersed in a polymer. For example, in one embodiment, the anti-biofilm agent may comprise silver sodium zirconium phosphate alloy dispersed in polyvinylpyrrolidone.

As shown in FIG. 3, the anti-fouling treatment of the present disclosure further includes a polymer over-layer 44. The polymer over-layer encapsulates the anti-biofilm agent within the treatment while still allowing the anti-biofilm agent to remain active in inhibiting bacterial attachment.

In one embodiment, the polymer over-layer 44 may comprise a chitosan, such as chitosan glycolate. Chitosan glycolate, for instance, has bacteriostatic properties, is biocompatible, and is non-cytotoxic. Of particular advantage, chitosan glycolate can be applied to the polymer substrate as a top layer at very thin thicknesses. In this manner, the anti-biofilm agent becomes fixed within the treatment while still remaining effective against bacterial attachment.

In other embodiments, the polymer over-layer may comprise a synthetic hydrogel such as for example polyvinyl pyrrolidone, polyacrylamide, hydroxyethyl methacrylate and others, and natural hydrogels of carbohydrate origin such as for example hyaluronic acid, chondroitin sulfate, dextran, and of protein origin such as albumin, collagen and other skin base membrane proteins.

Figure 4:
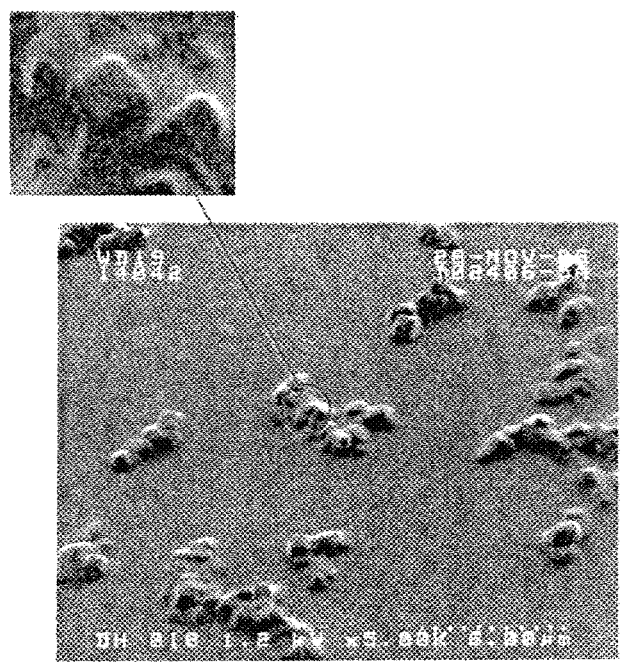
FIG. 4 is a magnified photograph of one embodiment of a treatment in accordance with the present disclosure.

Referring to FIG. 4, SEM photographs of an anti-fouling treatment in accordance with the present disclosure is shown. As shown, the anti-biofilm agent appears as projections on the surface of the polymer substrate. The anti-biofilm agent, however, is coated or encapsulated with a thin layer of the polymer over-layer.

When applied to a polymer substrate, the anti-fouling treatment of the present disclosure is very effective in reducing bacterial adhesion. For instance, in comparison to an identical polymer substrate that is not treated, the polymer substrate treated in accordance with the present disclosure can display at least a 1 Log reduction in bacterial adhesion, such as at least a 2 Log reduction, such as at least a 3 Log reduction, such as at least a 4 Log reduction.

The present disclosure may be better understood with reference to the following examples.

EXAMPLES

Polyurethane substrates made from PELLETHANE 2363 90A NAT polyurethane obtained from Lubrizol of Wickliffe, Ohio were coated with various coating formulations and then tested in a biofilm assay. The polyurethane substrates were in the shape of rectangular slabs having a length of about one inch and a width of about one-half inch. The below treatments were applied to one side of the rectangular slabs.

In particular, seven different polymer substrates (including three controls) were tested in the biofilm assay. The samples tested are as follows:

| Example | Substrate | Coating Formula and Method |
|---------|-----------|----------------------------|
| A | Polyurethane | None |
| B | Polyurethane | None |
| C | Polyurethane | Plasma oxidation only |
| D | Polyurethane | Formula D |
| E | Polyurethane | Formula E |
| F | Polyurethane | Formula F |
| G | Polyurethane | Formula G |

The following formulas were prepared in sub-sets to allow for better mixing of the ingredients and also to allow for sequential and controlled placement of chemistry where needed.

| Formula D | | |
|---|---|---|
| Ingredient | Wt % | Sub-set |
| Dimethylsulfoxide | 3.0 | 1 |
| 1-hydroxycyclohexyl phenyl ketone | 0.1 | |
| Acrylamido methyl propane sulfonic acid, sodium salt | 20.0 | |
| Water | 20.0 | 2 |
| Polyvinyl pyrrolidone | 1.0 | |
| Silver sodium hydrogen zirconium phosphate | 0.00 | |
| Water | 54.50 | 3 |
| Lactic Acid | 0.40 | |
| Chitosan glycolate | 1.00 | |

| Formula E | | |
|---|---|---|
| Ingredient | Wt % | Sub-set |
| Dimethylsulfoxide | 3.0 | 1 |
| 1-hydroxycyclohexyl phenyl ketone | 0.1 | |
| Acrylamido methyl propane sulfonic acid, sodium salt | 20.0 | |
| Water | 20.0 | 2 |
| Polyvinyl pyrrolidone | 1.0 | |
| Silver sodium hydrogen zirconium phosphate | 0.02 | |
| Water | 54.48 | 3 |
| Lactic Acid | 0.40 | |
| Chitosan glycolate | 1.00 | |

| Formula F | | |
|---|---|---|
| Ingredient | Wt % | Sub-set |
| Dimethylsulfoxide | 3.0 | 1 |
| 1-hydroxycyclohexyl phenyl ketone | 0.1 | |
| Acrylamido methyl propane sulfonic acid, sodium salt | 20.0 | |
| Water | 20.0 | 2 |
| Polyvinyl pyrrolidone | 1.0 | |
| Silver sodium hydrogen zirconium phosphate | 0.05 | |
| Water | 54.45 | 3 |
| Lactic Acid | 0.40 | |
| Chitosan glycolate | 1.00 | |

| Formula G | | |
|---|---|---|
| Ingredient | Wt % | Sub-set |
| Dimethylsulfoxide | 3.0 | 1 |
| 1-hydroxycyclohexyl phenyl ketone | 0.1 | |
| Acrylamido methyl propane sulfonic acid, sodium salt | 20.0 | |
| Water | 75.50 | 2 |
| Lactic Acid | 0.40 | |
| Chitosan glycolate | 1.00 | |

The silver sodium hydrogen zirconium phosphate used was obtained from Milliken of Spartanburg, S.C. and is sold under the tradename ALPHASAN RC2000. The silver sodium hydrogen zirconium phosphate particles had a particle size of less than about 5 microns. In particular, about 90% of the particles had a size of less than about 4 microns.

The following methods were used to treat each of the polyurethane substrates.

Samples C through G were all subject to plasma treatment. The plasma treatment was an RF plasma treatment and was as follows:

Generator: 13.56 MHz radio frequency (RF)
Gas: 100% oxygen
Pressure: 0.5 torr
Power: 125 watts
Time: 4 minutes Polyurethane substrates were systematically oxidized via RF plasma to allow for better wetting of the aqueous formulas and for more uniform coatings.

Example D

Sub-sets are prepared separately then mixed all together to a single formulation with random dispersion of ingredients. The dispersion is then used to coat the plasma treated substrate. Coating is performed by immersing the plasma treated substrate in the dispersion for about 10 minutes. After 10 minutes immersion, the substrate is removed from the dispersion and allowed to drip for about 5 minutes to remove excess coating. The coated sample is then exposed to a UV source for graft polymerization. The UV source operates at a wavelength of 254 nm and delivers energy of 5 Joules/cm$^2$ over a 5 minute period. After UV exposure and graft polymerization of the coated side, the sample is placed in distilled water for 30 minutes to remove excess monomer solution that may not have fully polymerized. The sample is then dried in an oven (coated side up) at about 80° C. for about 1 hour or until constant weight. The sample is stored in a polyester bag until testing.

Example E

Sub-sets are prepared separately and then applied to the substrate sequentially in successive distinct steps and in numerical order. Coated substrates are dried between each step. Drying between each step is carried in an oven at about 80° C. for about 20 minutes.

Step 1:

Coating is performed by immersing the plasma treated substrate in sub-set #1, for about 10 minutes. After 10 minutes immersion, the substrate is removed from the dispersion and allowed to drip for about 5 minutes to remove excess coating. The coated sample is then exposed to a UV source for graft polymerization. The UV source operates at a wavelength of 254 nm and delivers energy of 5 Joules/cm$^2$ over a 5 minute period. The sample is then dried in an oven at about 80° C. for about 20 minutes. After UV exposure and graft polymerization, the sample is placed in distilled water for 30 minutes to remove any excess monomer that may not have fully polymerized.

Step 2:

Sample from step 1 is immersed in sub-set #2 for about 10 minutes. Sample is then removed and let to drip for about 10 minutes to remove excess chemical. The sample is then dried in an oven at about 80° C. for about 20 minutes. The sample is then hung over a container and allowed to drip for about 10 minutes to remove excess chemical.

Step 3:

Sample from step 2 is immersed in subs-set #3 for about 10 minutes. The sample is then hung over a container and allowed to drip for about 10 minutes to remove excess chemical. The sample is then placed in an oven at about 80° C. for about 1 hour for final drying. After drying, the sample is stored in a polyester bag until testing.

Example F

Same procedure as Example E except that silver sodium hydrogen zirconium phosphate content in sub-set #3 is increased from 0.02 to 0.05 wt %.

Example G

Similar procedure as Example F but step of sub-set #2 is omitted, i.e. no silver sodium hydrogen zirconium phosphate and no polyvinyl pyrrolidone.

Samples were tested in a biofilm assay as follows:

Samples were incubated in the presence of ~10$^5$ colony forming units (CFU)/mL *Staphylococcus epidermidis* containing a 5% soil load for 6 hours at 37° C. The samples were then rinsed 8 times by dipping the sample in phosphate buffered saline (PBS) containing 0.1% Tween80 surfactant for two seconds to remove any loosely adhered bacteria. The samples were transferred to a 24 well plate containing an Alamar Blue solution and fluorescence was measured kinetically for 18 hours in a spectrophotometer. Fluorescence was measured in Relative Fluorescent Units (RFU's) and is proportional to the number of bacteria present.

Figure 5:
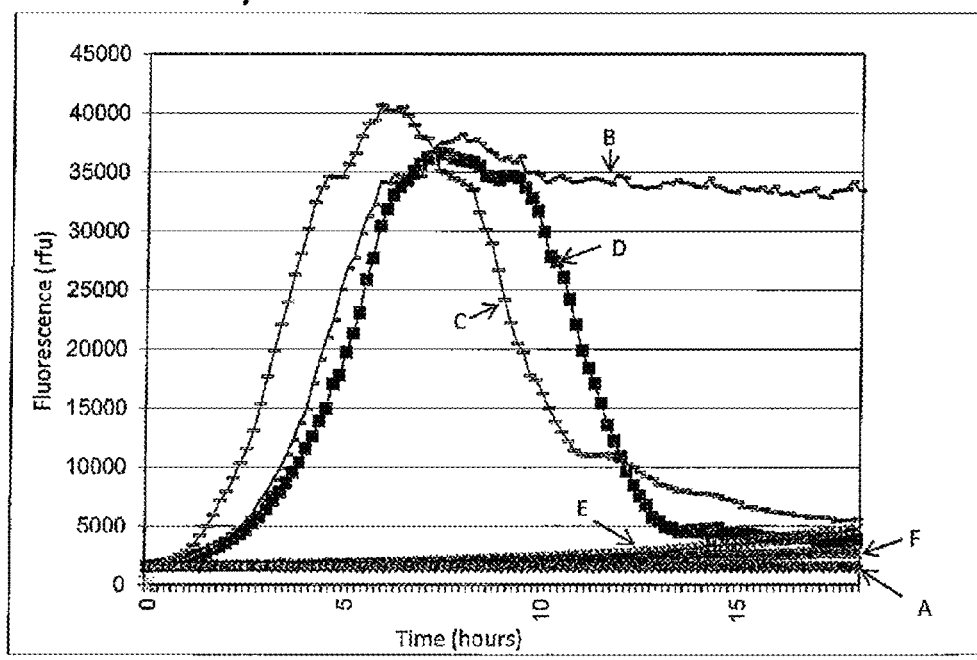
FIG. 5 is a graphical representation of the results obtained in the examples described below.

The results of the biofilm assay are illustrated in FIG. 5.

Examples B, G, E and F were then subjected to a biofilm assay in which the samples were incubated for 24 hours in the presence of *Pseudomonas aeruginosa* (strain ATCC 27853). The following results were obtained:

TABLE 1

| Biofilm Adherence Assay (24 hours, *P. aeruginosa* ATCC 27853) | | |
|---|---|---|
| Example | Planktonic AVG cfu/ml (Log$_{10}$) | Biofilm AVG cfu/cm$^2$ (log$_{10}$) |
| B (control) | 7.88 | 6.64 |
| G | 6.90 | 5.45 |
| E | 7.72 | <4.87 |
| F | Not detectable | <6.68 |

The results illustrated in the above table and on FIG. 5 can be summarized as follows:

Example A is polyurethane with no exposure to bacteria shows no fluorescence activity.

Example B (control) shows formation of biofilm.

Examples B, C and D show significant fluorescence signals and therefore indicate strong adhesion of bacterial biofilm (see FIG. 5).

Example E shows no significant fluorescence indicating no bacterial adhesion. Biofilm adherence assay (Table 1) shows that no planktonic bacteria are killed. Example E shows that bacterial biofilm was significantly reduced from 6.64 Log10 to <4.87 Log10 with no statistical change in level of planktonic bacteria. In Example E, the biofilm agent was present in the treatment in an amount of about 0.09% by weight based on the dried coating weight.

Example F also shows no fluorescence signal but data from Biofilm adherence assay shows total kill of bacteria (Table 1). Example F shows that all planktonic bacteria were killed due to higher level of anti-biofouling agent (silver sodium hydrogen zirconium phosphate). The anti-biofilm agent was present in the treatment in Example F in an amount of about 0.22% by weight based on the dried coating weight.

Example G which has no anti-biofouling agent (silver sodium hydrogen zirconium phosphate) also shows biofilm formation similar to example B.

Consequently, as shown above, in order to prevent biofilm adhesion without killing planktonic bacteria, the silver alloy particles, in one embodiment, can be present in an amount from about 0.005 to about 0.04% by weight, such as from about 0.01% to about 0.035% by weight.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An article including an anti-fouling treatment comprising:
    a polymer substrate having a first surface;
    a hydrogel polymer graft polymerized to the first surface of the polymer substrate, the hydrogel polymer including a top surface positioned opposite the first surface of the polymer substrate;
    an anti-biofilm agent associated with the hydrogel polymer, the anti-biofilm agent being present at the top surface; and
    a polymer over-layer positioned on the hydrogel polymer and encapsulating the anti-biofilm agent.

2. An article as defined in claim 1, wherein the anti-fouling treatment defines an exterior surface of the article and wherein the anti-biofilm agent is present within the anti-fouling treatment in an amount effective to inhibit adhesion of bacteria to the exterior surface of the article in relation to an untreated surface of the polymer substrate.

3. An article as defined in claim 1, wherein the anti-biofilm agent is present in the anti-fouling treatment in an amount from about 0.001% by weight to about 2% by weight.

4. An article as defined in claim 1, wherein the anti-biofilm agent is present in the anti-fouling treatment in an amount from about 0.001% by weight to about 0.2% by weight.

5. An article as defined in claim 1, wherein the first surface of the polymer substrate has been treated with a plasma.

6. An article as defined in claim 1, wherein the hydrogel polymer has been subjected to irradiation in an amount sufficient to cause grafting with the first surface of the polymer substrate.

7. An article as defined in claim 1, wherein the anti-biofilm agent is located between the hydrogel polymer and the polymer over-layer and wherein the polymer over-layer defines the exterior surface of the anti-fouling treatment.

8. An article as defined in claim 1, wherein the hydrogel polymer is anionic and the polymer over-layer is cationic.

9. An article as defined in claim 1, wherein the polymer over-layer comprises chitosan.

10. An article as defined in claim 1, wherein the polymer over-layer comprises chitosan glycolate.

11. An article as defined in claim 1, wherein the anti-biofilm agent comprises a metal or a metal alloy.

12. An article as defined in claim 1, wherein the anti-biofilm agent comprises a silver alloy.

13. An article as defined in claim 7, wherein the anti-biofilm agent comprises silver sodium zirconium phosphate dispersed in polyvinylpyrrolidone.

14. An article as defined in claim 1, wherein the hydrogel polymer is formed from a monomer comprising acrylamido methyl propane sulfonic acid or a salt thereof.

15. An article as defined in claim 1, wherein the hydrogel polymer is formed from one or more monomers comprising N,N-dimethylaminoethyl acrylate dimethyl sulfate quaternary, dimethyl amino ethyl methacrylate, acrylic acid, methacrylic acid, acrylamide, N-(3-aminopropyl) methacrylamide hydrochloride, hydroxyethyl methacrylate, styrene sulfonic acid, potassium sulfopropyl acrylate, di methylacrylamide, dimethyl amino ethyl methacrylate or their salts.

16. An article as defined in claim 1, wherein the hydrogel polymer further comprises a crosslinking agent and an initiator.

17. An article as defined in claim 1, wherein the polymer over-layer has a thickness of less than about 100 microns.

18. A respiratory device including a tubular structure defining a lumen, the tubular structure comprising the article defined in claim 1, wherein the anti-fouling treatment comprises a lining for the lumen.

19. An article as defined in claim 1, wherein the anti-biofilm agent is present in the anti-fouling treatment in an amount effective to inhibit adhesion of bacteria to the first surface of the article without substantially killing planktonic bacteria.

20. A catheter comprising:
    a tubular structure comprised of a polymer, the tubular structure defining a lumen, the tubular structure including an anti-fouling lining for the lumen, the anti-fouling lining comprising a hydrogel polymer graft polymerized to an interior surface of the tubular structure, the hydrogel polymer including a top surface positioned opposite the interior surface of the polymer substrate;
    an anti-biofilm agent associated with the hydrogel polymer, the anti-biofilm agent being present at the top surface; and
    a polymer over-layer positioned on the hydrogel polymer and encapsulating the anti-biofilm agent; and
    wherein the anti-fouling treatment defines an exterior surface of the catheter and wherein the anti-biofilm agent is present within the anti-fouling treatment and wherein the anti-biofilm agent is present in an amount effective to inhibit adhesion of bacteria to the exterior surface of the catheter.

21. A catheter as defined in claim 20, wherein the catheter comprises a tracheal tube.

22. A catheter as defined in claim 20, wherein the hydrogel polymer is formed from a monomer comprising acrylamido methyl propane sulfonic acid or a salt thereof, the anti-biofilm agent comprising a metal or a metal alloy, and wherein the polymer over-layer comprises chitosan glycolate, the polymer over-layer having a thickness of less than 50 microns.

23. A catheter as defined in claim 20, wherein the tubular structure is comprised of a polyurethane, a polyvinylchloride, or a silicone.

24. A catheter as defined in claim 20, wherein the interior surface of the tubular structure has been plasma treated prior to being graft polymerized with the hydrogel polymer.

* * * * *